United States Patent [19]

Tuszynski et al.

[11] Patent Number: 5,367,059
[45] Date of Patent: Nov. 22, 1994

[54] CYS-SER-VAL-THR-CYS-GLY SPECIFIC TUMOR CELL ADHESION RECEPTOR

[75] Inventors: George P. Tuszynski, Williamstown, N.J.; Jacob Eyal, Baltimore; Bruce K. Hamilton, Silver Spring, both of Md.

[73] Assignees: W. R. Grace & Co.-Conn., New York, N.Y.; The Medical College of PA, Philadelphia, Pa.

[21] Appl. No.: 883,659

[22] Filed: May 14, 1992

[51] Int. Cl.5 .............................................. C07K 15/14
[52] U.S. Cl. .................................... 530/395; 530/350
[58] Field of Search ................................ 530/350, 395

[56] References Cited

U.S. PATENT DOCUMENTS 5,190,920  3/1993  Eyal et al. ............................. 514/17
5,192,744  3/1993  Bouck et al. ........................... 514/8

OTHER PUBLICATIONS

Asch et al., "Isolation of Thrombospondin Membrane Receptor", J Clin Invest., vol. 79, 1987 pp. 1054–1061.
Asch et al., "Thrombospondin sequence motif . . . ", Biochem & Biophy. Commun., vol. 182, No. 3, Feb. 1992, pp. 1208–1217.
Yabkowitz, et al., "Human Carcinoma Cells . . . ", Cancer Research, vol. 51, Jul. 1991, pp. 3648–3656.
Yabkowitz et al, "Human Carcinoma Cells Express Receptors . . . " Cancer Research, vol. 51, Mar. 1991, pp. 1645–1650.
McGregor, et al., "Rapid Purification & Partial Characterization . . . " J of Biol. Chem., vol. 264, No. 1, 1989, pp. 501–506.

Primary Examiner—Michael G. Wityshyn
Assistant Examiner—C. Sayala
Attorney, Agent, or Firm—Bharat C. Gandhi

[57] ABSTRACT

The present invention provides a cell matrix receptor specific for the Cys Ser Val Thr Cys Gly (SEQ ID NO: 1) region of thrombospondin. Also provided are purification, cloning and expression methods. Antibodies directed against the receptor protein are useful in numerous diagnostic, prophylactic and therapeutic areas.

4 Claims, 2 Drawing Sheets

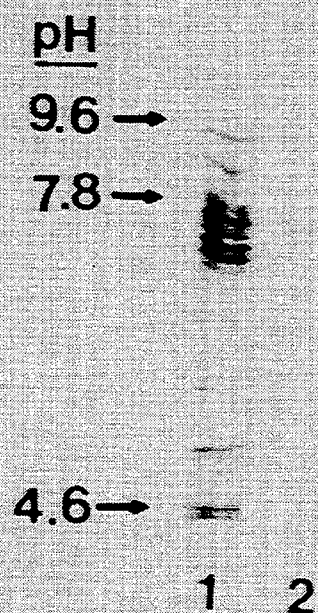

CYS-SER-VAL-THR-CYS-GLY SPECIFIC TUMOR CELL ADHESION RECEPTOR

TECHNICAL FIELD

A cell matrix receptor, specific for the Cys Ser Val Thr Cys Gly (SEQ ID NO: 1) region of thrombospondin expressed on the surface of tumor cells, is provided along with methods for purifying the CSVTCG-specific receptor. The Cys Ser Val Thr Cys Gly (SEQ ID NO: 1)-specific receptor and antibodies to the receptor are useful in numerous diagnostic and therapeutic conditions, such as use as ligands in binding assays for cancer diagnosis and in cancer management.

BACKGROUND OF THE INVENTION

The basement membrane is a ubiquitous, specialized type of extracellular matrix separating organ parenchymal cells from interstitial collagenous stroma. Interaction of cells with this matrix is an important aspect of both normal and neoplastic cellular processes. Normal cells appear to require an extracellular matrix for survival, proliferation and differentiation, while migratory cells, both normal and neoplastic, must traverse the basement membrane in moving from one tissue to another. In particular, metastatic cancer cells arising in squamous or glandular epithelium must traverse the basement membrane to enter the circulatory and lymphatic systems (intravasation); the circulating neoplastic cells are typically arrested in the capillary beds of an organ, invade the blood vessel walls, and penetrate the basement membrane to extravascular tissue (extravasation), where a secondary neoplasm is then established. The mechanisms of cellular interaction with the basement membrane are thus of great interest.

The interaction of cells with extracellular matrices is dependent upon the ability of the cells to attach themselves to the matrix; it is known that this attachment may be mediated by specific glycoproteins which typically bind cells to discrete collagen types present in the matrix. Fibronectin-mediated attachment of fibroblasts, myoblasts, and smooth muscle cells to interstitial type I and type III collagen, and chondronectin-mediated attachment of chondrocytes to type II cartilage collagen, are exemplary.

It has been found that the attachment of both normal and neoplastic cells to the basement membranes is similarly mediated. The primary constituents of the basement membrane are type IV collagen, glycoproteins and proteoglycans. The glycoprotein laminin mediates the attachment of both epithelial and neoplastic cells to the basement membrane, binding the cells to type IV collagen. Since, as previously noted, metastasizing tumor cells must traverse basement membranes at multiple stages in the metastatic process, and since the first step in this process is tumor cell attachment to the basement membrane, the elucidation of this mechanism and the corollary characterization of specific attachment factors which promote or inhibit tumor cell attachment to this membrane has important implications for cancer diagnosis and management.

A number of studies show that TSP can bind to multiple cell surface receptors on the same cell or bind to different receptors on different cells. For example, platelets can bind TSP through $GPII_b$-$IIIa$, $GPI_a$-$II_a$ (Karczewski et al., *J. Biol. Chem.* (1989) 264:21332–21326 and Tuszynski et al., *J. Clin. Invest.* (1991) 87:1387–1394), and the vitronectin-receptor (Tuszynski et al., *Exp. Cell Res.* (1989) 182:481). Smooth muscle cells, endothelial cells, U937 monocyte-like cells, and melanoma cells can bind TSP through a vitronectin-like receptor. Squamous cell carcinoma bind TSP through a Mr 80,000/105,000 that is not an integrin or GPIV (Yabkowitz et al., *Cancer Res.* (1991) SI:3648–3656).

Receptors for other extracellular matrix proteins have been isolated. Liotta et al. (U.S. Pat. No. 4,565,789) describe the isolation of a laminin receptor. Mecham et al. (J. Biol. Chem. (1989) 264:16652–7) describe an elastin receptor which exhibits structural and functional similarity to the 67 kd laminin receptor. CD36 has been implicated as binding the Cys Ser Val Thr Cys Gly (SEQ ID NO: 1) sequence of thrombospondin (Asch et al., Biochem. Biophys. Res. Comm. (1992) 182:1208–1217). However, CD36 is an 88 kd protein. The Cys Ser Val Thr Cys Gly (SEQ ID NO: 1)-specific receptor of the present invention is different from these previously isolated extracellular matrix protein receptors.

SUMMARY OF THE INVENTION

It is an object of the present invention to provide an isolated receptor having specific binding affinity for the Cys Ser Val Thr Cys Gly (SEQ ID NO: 1)-specific region of thrombospondin (TSP). The receptor is cell surface exposed. The receptor has a molecular weight as analyzed on SDS-gels of about 50 kd under non-reducing conditions and as two protein bands of molecular weight of about 50 kd and about 60 kd under reducing conditions. The receptor is a glycoprotein made up of two subunits linked by intrachain disulfide bonds which has an isoelectric focusing point of about pH 7.1–7.5.

Another object of the present invention is to provide a method of purifying a CSVTCG-specific receptor. The method for purifying the CSVTCG-specific receptor protein comprises:

a) preparing a cell extract from a tumor cell line having Cys Ser Val Thr Cys Gly (SEQ ID NO: 1)-specific receptors;

b) passing said cell extract through a chromatographic column containing immobilized Cys Ser Val Thr Cys Gly (SEQ ID NO: 1) peptides under conditions whereby said Cys Ser Val Thr Cys Gly (SEQ ID NO: 1)-specific receptor protein binds to said immobilized Cys Ser Val Thr Cys Gly (SEQ ID NO: 1) peptide; and c) eluting bound receptor protein from said column to provide purified receptor.

Still another object of the present invention is to provide antibodies, and cell lines producing such antibodies, which bind an epitope on the Cys Ser Val Thr Cys Gly (SEQ ID NO: 1)-specific receptor.

A further object of the present invention provides a method for diagnosing a carcinoma by reacting a sample of a tissue suspected to have a carcinoma with a CSVTCG-specific receptor specific antibody and determining binding between the tissue and the antibody.

A further objective is to provide pharmaceutical compositions which contain a Cys Ser Val Thr Cys Gly (SEQ ID NO: 1)-specific receptor antibody together with a pharmaceutically acceptable liquid, gel or solid carrier. Administration of therapeutically effective doses of the compositions can provide effective enhancement or inhibition of thrombospondin-like activity to animals, particularly vertebrates such as mammalian and avian hosts.

Another object of the invention is to provide DNA molecules encoding the Cys Ser Val Thr Cys Gly (SEQ ID NO: 1)-specific receptor protein and methods of producing Cys Ser Val Thr Cys Gly (SEQ ID NO: 1)-specific receptor protein by recombinant DNA methods.

BRIEF DESCRIPTION OF THE DRAWINGS

FIG. 2 is an isoelectric focusing gel, showing the isoelectric point of the Cys Ser Val Thr Cys Gly (SEQ ID NO: 1)-specific receptor protein in Lane 2.

DETAILED DESCRIPTION OF THE INVENTION

Figure 1:
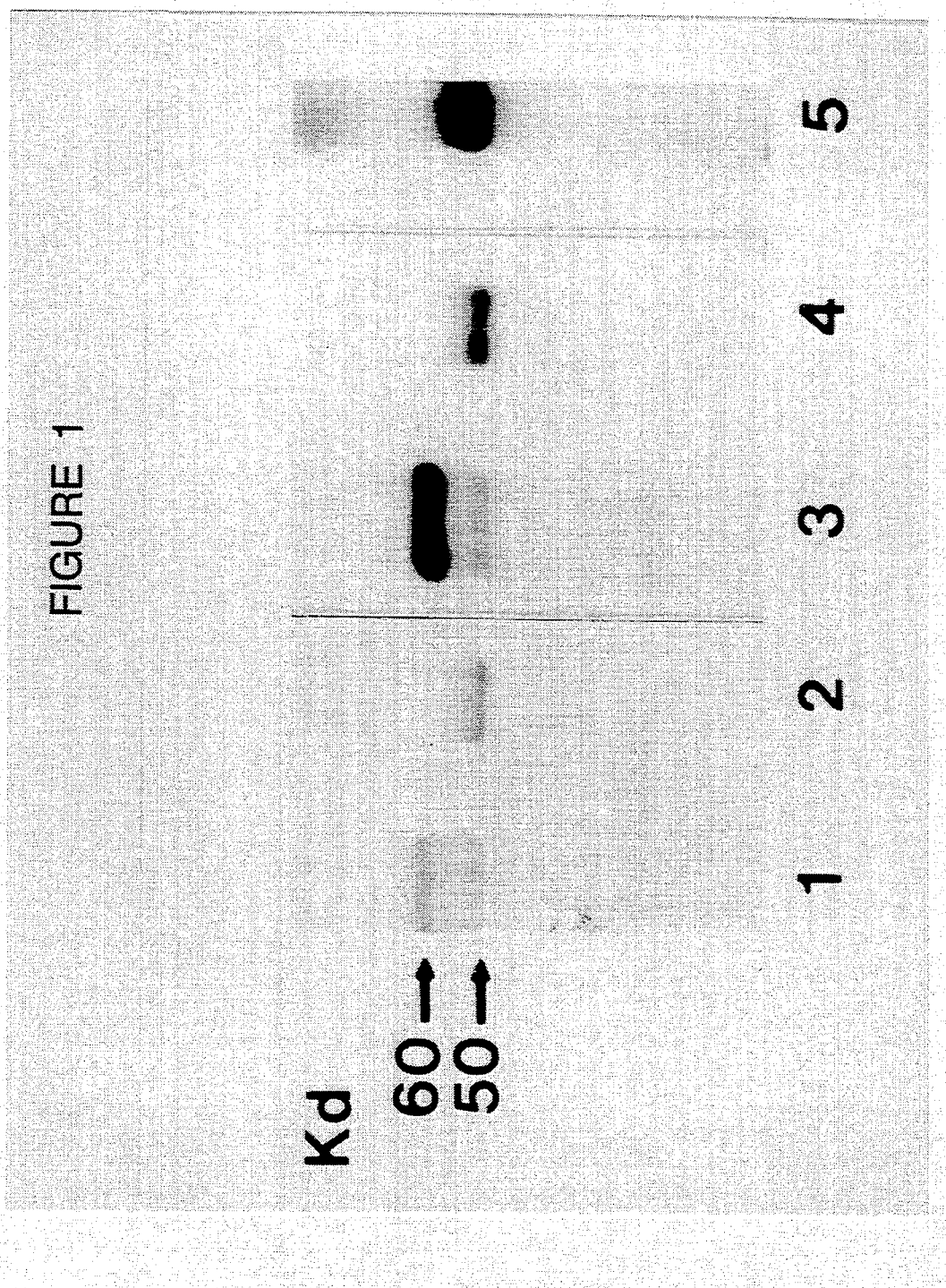
FIG. 1 is an SDS-PAGE gel of the CSVTCG-specific receptor protein. Lane 1 is non-reduced protein (stained). Lane 2 is reduced protein (stained). Lane 3 is non-reduced protein (labelled). Lane 4 is reduced protein (labelled). Lane 5 is non-reduced surface-labelled protein.

The present invention provides a purified thrombospondin (TSP) receptor protein in a usable form. The receptor is specific for the Cys Ser Val Thr Cys Gly (SEQ ID NO: 1) region of thrombospondin. The receptor protein can be employed, for example, for producing antibodies which will be useful in numerous therapeutic areas, including cancer diagnosis or management. Computer modeling of the Cys Ser Val Thr Cys Gly (SEQ ID NO: 1)-specific receptor binding site may also aid in the design of new compounds which block or bind the Cys Ser Val Thr Cys Gly (SEQ ID NO: 1)-specific receptor site in vivo.

A. Definitions

"Cys Ser Val Thr Cys Gly (SEQ ID NO: 1)-specific receptor protein", "Thrombospondin receptor protein" or "TSP receptor" or "receptor" refers to a native thrombospondin receptor protein from any mammalian source, including, but not limited to, human and mouse which demonstrates a specific binding affinity for the peptide Cys Ser Val Thr Cys Gly (SEQ. ID No: 1). The term also includes synthetic TSP receptor protein, i.e. protein produced by recombinant means or direct chemical synthesis. TSP receptor protein is a protein found in platelets, endothelial cells, epithelial (lung) cells; smooth muscle cells, fibroblasts, keratinocytes, monocyte macrophages, glial cells and most particularly cancer tissues, including, but not limited to, melanoma cells and lung carcinoma cells.

"Thrombospondin-like activity" is defined herein as any activity that mimics the known biological activities of thrombopondin. These activities include cell-adhesion promoting activity, cell mitogenic activity, cell chemotactic activities, and hemostatic activities and any activities that derive from these activities such as tumor cell, microbial, or parasite metastasis activity, platelet aggregating activity, fibrinolytic activity and immune modulation.

"Antimetastatic activity" is defined herein as the ability to prevent or greatly reduce the extent or size of tumor cell metastasis, or inhibit or cause regression of primary solid tumors.

"Atherosclerosis activity" is defined herein as the capacity of thrombospondin to either promote or inhibit atherosclerotic lesion formation. The atherosclerotic lesion is defined as the degenerative accumulation of lipid-containing materials, especially in arterial walls.

"Antimalaria activity" is defined herein as the ability to inhibit either the cytoadherence of malarial-infected red blood cells to endothelial cells, the malarial sporozoite recognition and entry into hepatocytes, or the malarial merozoite recognition and entry into red blood cells. Antimalarial activity can be demonstrated in the form of a vaccine or a therapeutic that blocks cytoadherence.

"Antithrombotic activity" is defined herein as the ability to either inhibit the aggregation of platelets or to antagonize the formation of a thrombus.

"Thrombolytic activity" is defined herein as the ability to disrupt the structure of a thrombus.

"Angiogenesis activity" is defined herein as the ability to inhibit or enhance the formation of blood vessels or lymph vessels.

"Growth factor activity" is defined herein as the ability to inhibit or promote cell proliferation.

"Cell adhesion activity" is defined herein as the ability to promote or inhibit the attachment of cells, preferably mammalian cells, to a substrate.

B. Preferred Embodiments

The preferred receptor protein of the present invention is derived from cancer tissues, such as melanoma cells or lung carcinoma cells. Analysis of the Cys Ser Val Thr Cys Gly (SEQ ID NO: 1)-specific receptor by sodium dodecylsulfate polyacrylamide gel electrophoresis (SDS-PAGE) shows that the receptor has an apparent molecular weight of 50 kd under non-reducing conditions. In some preparations, small amounts of dimers could be observed with molecular weights of greater than 100 kd. Under reducing conditions, the protein migrates as two major polypeptide bands spaced closely together with apparent molecular weights of 50 and 60 kd. This is consistent with the interpretation that the protein consists of two interchain disulfide-linked polypeptide chains that assume a more compact configuration when disulfide bonded.

The protein does not crossreact with antibodies against integrins laminin, or GPIV.

The Cys Ser Val Thr Cys Gly (SEQ ID NO: 1)-specific receptor protein is a glycoprotein since in binds galactose, mannose, and glucosamine specific lectins. Consistent with the presence of carbohydrate is the high 260 nm absorbance of the purified receptor protein.

The Cys Ser Val Thr Cys Gly (SEQ ID NO: 1)-specific receptor protein has an isoelectric focus point of about pH 7.1–7.5.

To characterize the purified native CSVTCG-specific receptor further its activity as a receptor in vitro was studied. The receptor interacts with thrombospondin in an ion dependent manner, but does not interact with fibronectin or bovine serum albumin.

One of ordinary skill in the art can use standard methods to determine the amino acid composition and protein sequence of the isolated Cys Ser Val Thr Cys Gly (SEQ ID NO: 1)-specific receptor. For example, the amino acid sequence of the receptor can be determined from the purified protein by repetitive cycles of Edman degradation, followed by amino acid analysis by HPLC. Other methods of amino acid sequencing are also known in the art.

Purification of Cys Ser Val Thr Cys Gly (SEQ ID NO: 1)-specific receptor protein from cells comprises two basic steps: preparation of the cells and purification of the receptor by affinity chromatography. Preferred cell sources included mouse melanoma cells and human lung carcinoma cells which are readily available to the public. Cultured cells have the additional benefit of being relatively protease-free compared to most tissue sources. This facilitates stabilization and purification of active receptor protein.

A cell extract is prepared and passed through a chromatographic column containing immobilized Cys Ser Val Thr Cys Gly (SEQ ID. NO: 1) peptides under conditions where the receptor will bind to the Cys Ser Val Thr Cys Gly (SEQ ID NO: 1) peptide. The Cys Ser Val Thr Cys Gly (SEQ ID NO: 1)-specific receptor is then eluted from the column in purified form.

One of skill in the art can clone and sequence the cDNA and gene for the Cys Ser Val Thr Cys Gly (SEQ ID NO: 1)-specific receptor protein. Cloning can be done by employing antibodies against the Cys Ser Val Thr Cys Gly (SEQ ID NO: 1)-specific receptor and expression libraries or once an amino acid sequence is determined, oligonucleotide probes which contain the codons for a portion of the determined amino acid sequence are prepared and used to screen DNA libraries for genes encoding the receptor protein. The basic strategies for preparing antibodies or oligonucleotide probes and DNA libraries, as well as their screening by antibody or nucleic acid hybridization, are well known to those of ordinary skill in the art. See, e.g., *DNA CLONING: VOLUME I* (D. M. Glover ed. 1985): *NUCLEIC ACID HYBRIDIZATION* (B. D. Hames and S. J. Higgins eds. 1985): *OLIGONUCLEOTIDE SYNTHESIS* (M. J. Gate ed. 1984): T. Maniatis, E. F. Frisch & J. Sambrook, *MOLECULAR CLONING: A LABORATORY MANUAL* (1982).

First, a DNA library is prepared. The library can consist of a genomic DNA library from a selected mammal, such as a human. Human genomic libraries are known in the art. See, e.g., Lawn et al., (1978) *Cell* 15:1157-1174. DNA libraries can also be constructed of cDNA prepared from a poly-A RNA (mRNA) fraction by reverse transcription. See, e.g., U.S. Pat. Nos. 4,446,235; 4,440,859; 4,433,140; 4,431,740; 4,370,417; 4,363,877. The mRNA is isolated from a cell line or tissue known to express the receptor protein. Cell lines or tissue expressing Cys Ser Val Thr Cys Gly (SEQ ID NO: 1)-specific receptor protein are described herein. cDNA (or genomic DNA) is cloned into a vector suitable for construction of a library. A preferred vector is a bacteriophage vector, such as phage λ. The construction of an appropriate library is within the skill of the art.

Once the library is constructed, antibodies or oligonucleotides to probe the library are prepared and used to isolate the desired Cys Ser Val Thr Cys Gly (SEQ ID NO: 1)-specific receptor protein gene. The antibodies or oligonucleotides are synthesized by any appropriate method. For oligonucleotide preparation, the particular nucleotide sequences selected are chosen so as to correspond to the codons encoding a known amino acid sequence from the receptor protein. Since the genetic code is redundant, it will often be necessary to synthesize several oligonucleotides to cover all, or a reasonable number, of the possible nucleotide sequences which encode a particular region of the protein. Thus, it is generally preferred in selecting a region upon which to base the probes, that the region not contain amino acids whose codons are highly degenerate. It may not be necessary, however, to prepare probes containing codons that are rare in the mammal from which the library was prepared. In certain circumstances, one of skill in the art may find it desirable to prepare probes that are fairly long, and/or encompass regions of the amino acid sequence which would have a high degree of redundancy in corresponding nucleic acid sequences, particularly if this lengthy and/or redundant region is highly characteristic of the receptor protein. It may also be desirable to use two probes (or sets of probes), each to different regions of the gene, in a single hybridization experiment. Automated oligonucleotide synthesis has made the preparation of large families of probes relatively straightforward. While the exact length of the probe employed is not critical, generally it is recognized in the art that probes from about 14 to about 20 base pairs are usually effective. Longer probes of about 25 to about 60 base pairs are also used.

The selected oligonucleotide probes are labelled with a marker, such as a radionucleotide or biotin using standard procedures. The labelled set of probes is then used in the screening step, which consists of allowing the single-stranded probe to hybridize to isolated ssDNA from the library, according to standard techniques. Either stringent or permissive hydridization conditions could be appropriate, depending upon several factors, such as the length of the probe and whether the probe is derived from the same species as the library, or an evolutionarily close or distant species. The selection of the appropriate conditions is within the skill of the art. See generally, *NUCLEIC ACID HYDRIDIZATION*, supra. The basic requirement is that hydridization conditions be of sufficient stringency so that selective hybridization occurs: i.e., hybridization is due to a sufficient degree of nucleic acid homology (e.g., at least about 70-75%), as opposed to nonspecific binding. Once a clone from the screened library has been identified by positive hybridization, it can be confirmed by restriction enzyme analysis and DNA sequencing that the particular library insert contains a gene for the receptor protein.

Alternatively, a DNA coding sequence for Cys Ser Val Thr Cys Gly (SEQ ID NO: 1)-specific receptor subunit can be prepared synthetically from overlapping oligonucleotides whose sequence contains codons for the amino acid sequence of the receptor protein. Such oligonucleotides are prepared by standard methods and assembled into a complete coding sequence. See, e.g., Edge, (1981) *Nature* 292:756; Nambair et al., (1984) *Science* 223:1299; Jay et al., (1984) *J. Biol. Chem.* 259:6311.

A DNA molecule containing the coding sequence for Cys Ser Val Thr Cys Gly (SEQ ID NO: 1)-specific receptor protein can be cloned in any suitable vector and thereby maintained in a composition substantially free of vectors that do not contain the coding sequence of the Cys Ser Val Thr Cys Gly (SEQ ID NO: 1)-specific receptor gene (e.g., other library clones). Numerous cloning vectors are known to those of skill in the art, and the selection of an appropriate cloning vector is a matter of choice. Examples of recombinant DNA vectors for cloning and the host cells which they transform include bacteriophage λ (*E. coli*). pBR322 (*E. coli*), pACYC177 (*E. coli*), pKT230 (gram-negative bacteria), pGV1106 (gram-negative bacteria), pLAFR1 (gram-negative bacteria), pME290 (non-*E. coli* gram-negative bacteria), pHV14 (*E. coli* and *Bacillus subtilis*), pBD9 (Bacillus), pIJ61 (Streptomyces), pUC6 (Streptomyces), actinophage ψC31 (Streptomyces), YIp5 (yeast), YCp19 (yeast), and bovine papilloma virus (mammalian cells). See generally, *DNA CLONING:*

VOLUMES I & II, supra; MOLECULAR CLONING: A LABORATORY MANUAL, supra.

In one embodiment of the present invention, the coding sequence from Cys Ser Val Thr Cys Gly (SEQ ID NO: 1)-specific receptor protein gene is placed under the control of a promoter, ribosome binding site (for bacterial expression) and, optionally, an operator (collectively referred to herein as "control" sequences), so that the DNA sequence encoding the receptor protein (referred to herein as the "coding" sequence) is transcribed into RNa in the host cell transformed by the vector. The coding sequence may or may not contain a signal peptide or leader sequence.

The recombinant vector is constructed so that the receptor protein coding sequence is located in the vector with the appropriate control sequences, the positioning and orientation of the receptor coding sequence with respect to the control sequences being such that the coding sequence is transcribed under the control of the control sequences (i.e., by RNA polymerase which attaches to the DNA molecule at the control sequences). The control sequences may be ligated to the coding sequence prior to insertion into a vector, such as the cloning vectors described above. Alternatively, the coding sequence can be cloned directly into an expression vector which already contains the control sequence and an appropriate restriction site downstream from control sequences. For expression of the receptor protein coding sequence in procaryotes and yeast, the control sequences will be heterologous to the coding sequence. If the host cell is a procaryote, it is also necessary that the coding sequence be free of introns: e.g., cDNA. If the selected host cell is a mammalian cell, the control sequences can be heterologous or homologous to the receptor protein coding sequence, and the coding sequence can be genomic DNA containing introns or cDNA. Either genomic or cDNA coding sequence may be expressed in yeast. A number of procaryotic expression vectors are known in the art.

Recombinant Cys Ser Val Thr Cys Gly (SEQ ID NO: 1)-specific receptor protein can be produced by growing host cells transformed by the expression vector described above under conditions whereby the Cys Ser Val Thr Cys Gly (SEQ ID NO: 1)-specific receptor protein is produced. Cys Ser Val Thr Cys Gly (SEQ ID NO: 1)-specific receptor protein is then isolated from the host cells and purified. If the expression system secretes the receptor protein into growth media, the receptor protein can be purified directly from cell-free media. If the receptor protein is not secreted, it is isolated from cell lysates. The selection of the appropriate growth conditions and recovery methods are within the skill of the art.

Either native or synthetic Cys Ser Val Thr Cys Gly (SEQ ID NO: 1)-specific receptor protein can be used to produce antibodies, both polyclonal and monoclonal. If polyclonal antibodies are desired, purified receptor protein is used to immunize a selected mammal (e.g., mouse, rabbit, goat, horse, etc.) and serum from the immunized animal later collected and treated according to known procedures. Compositions containing polyclonal antibodies to a variety of antigens in addition to the receptor protein can be made substantially free of antibodies which are not anti-receptor protein antibodies by passing the composition through a column to which receptor has been bound. After washing, polyclonal antibodies to the receptor are eluted from the column. Monoclonal anti-receptor protein antibodies can also be readily produced by one skilled in the art. The general methodology for making monoclonal antibodies by hybridomas is well known. Immortal, antibody-producing cell lines can also be created by techniques other than fusion, such as direct transformation of B lymphocytes with oncogenic DNA, or transfection with Epstein-Barr virus. (See e.g., M. Schreier et al., "Hybridoma Techniques" (1980); Hammerling et al., "Monoclonal Antibodies and T-Cell Hybridomas" (1981) Kennett et al., "Monoclonal Antibodies" (1980)).

By employing TSP receptor protein (native or synthetic) as an antigen in the immunization of the source of the B-cells immortalized for the production of monoclonal antibodies, a panel of monoclonal antibodies recognizing epitopes at different sites on the receptor protein molecule can be obtained. Antibodies which recognize an epitope in the binding region of the receptor protein can be readily identified in competition assays between antibodies and TSP. Such antibodies could have therapeutic potential if they are able to block the binding of TSP to its receptor in vivo without stimulating the physiological response associated with TSP peptide binding.

C. Administration

The antibodies of the present invention can mediate thrombospondin-like activity in the intact animal. The antibodies of the present invention and compositions containing them which are shown to have the physiological effect of inhibiting or mimicing the effect of intact thrombospondin find use in numerous therapeutic and prophylactic applications, such as cancer therapy, atherosclerosis, malaria treatment or prevention, thrombotic or thrombolytic conditions, angiogenesis, or cell attachment.

Thus the present invention also provides compositions containing an effective amount of the antibodies of the present invention, including the nontoxic addition salts, amides and esters thereof, which may, alone, serve to provide the above-recited therapeutic benefits. Such compositions can also be provided together with physiologically tolerable liquid, gel or solid diluents, adjuvants and excipients.

These antibodies and compositions can be administered to animals for veterinary use, such as with domestic animals, and clinical use in humans in a manner similar to other therapeutic antibody agents.

The compositions are conventionally administered parenterally, by injection, for example, either subcutaneously or intravenously. Additional formulations which are suitable for other modes of administration include suppositories, intranasal aerosols, and, in some cases, oral formulations.

While not wishing to be bound by any theory, it is believed that the compositions of the invention act as agonists or antagonists to native thrombospondin. These antibodies are also believed to act as agonists or antagonists to circumsporozoite protein, thrombospondin related anonymous protein, and properdin complement protein.

D. Use

As stated previously, the antibodies directed against the Cys Ser Val Thr Cys Gly (SEQ ID NO: 1)-specific receptor of the invention can be used in a variety of diagnostic, biological, prophylactic or therapeutic areas. It is contemplated that these antibodies are useful in prevention or treatment of any disease state or conditions wherein thrombospondin-like activity plays a role. These disease states and conditions include, but are not limited to, metastasis, atherosclerosis, malaria, thrombotic conditions, and angiogenesis. Antibodies are also useful as diagnostic reagents, therapeutics, or carriers of other compounds. The antibodies can also be used in biomedical devices.

Numerous in vitro and in vivo assays can be used to demonstrate that the antibodies effect thrombospondin-like activity. These assays include, but are not limited to, cell adhesion assays, platelet aggregation assays and cell proliferation assays.

METASTASIS

Metastasis is the spread of disease from one part of the body to another unrelated to it, as in the transfer of the cells of a malignant tumor by way of the bloodstream or lymphatics. It is believed that metastasis is effected through a cascade mechanism which includes adhesion of tumor cells to endothelium, retraction of the endothelium, matrix degradation of the basement membrane and invasion of the tumor cells into the bloodstream. Intervention at any phase in this cascade could be beneficial to the treatment or prevention of metastatic cancers.

The native thrombospondin molecule has been shown to potentiate tumor cell metastasis (Tuszynski et al., Cancer Research (1987) 47:4130-4133). The mechanisms by which the thrombospondin potentiation occurs are not presently well understood.

Antimetastasis activity is characterized by the ability of the compounds to bind to melanoma cells in vitro (Tuszynski et al., Anal. Bio. (1990) 184:189-91), and the ability to reduce the size and number of tumor colonies in vivo (Tuszynski et al. Cancer Research (1987) 47:4130-4133).

The antibodies of this invention are useful as antimetastatic agents, particularly useful as anti-pulmonary metastatic agents. These antibodies inhibit the adhesion of metastatic tumor cells, particularly those which are responsive to thrombospondin. The antibodies also reduce tumor colony number as well as tumor colony size. A particular advantage of the antibodies is a long circulating half-life.

There are a number of mechanisms by which such antimetastatic activity can be occurring. The antibodies can be cytotoxic, or inhibit cell proliferation. As inhibitors of cell proliferation, the antibodies can act to 1) inhibit mitogenesis, 2) inhibit angiogenesis, or 3) activate the complement pathway and the associated killer cells.

The antibodies of the invention can also find use in biomedical devices. Since the antibodies have the ability to promote the attachment of metastatic tumor cells, it is possible to coat a biomedical device with the antibodies to effect the removal of circulating tumor cells from blood or lymph. The biomedical device is also useful to trap hepatomas.

Another use of the antibodies is as a carrier to target toxins, drugs, hormones or imaging agents to metastatic tumor cells for diagnostic or therapeutic purposes. These carriers would also bind to hepatomas.

ATHEROSCLEROSIS

Atherosclerosis is a disease state which is characterized by the deposition of small fatty nodules on the inner walls of the arteries, often accompanied by degeneration of the affected areas.

Atherosclerosis activity is characterized by the capacity of the antibodies to inhibit the development of aortic lesions in rabbits fed a high cholesterol diet.

MALARIA

Malaria is an infectious disease caused by any of various protozoans (genus Plasmodium) that are parasitic in the red blood corpuscles and are transmitted to mammals by the bite of an infected mosquito. The antibodies of the invention can be used as therapeutic agents to block cytoadherence.

Antimalarial activity is characterized by the ability to inhibit either the cytoadherence of malarial-infected red blood cells to endothelial cells, the malarial sporozoite recognition and entry into hepatocytes, or the malarial merozoite recognition and entry into red blood cells.

THROMBOTIC CONDITIONS

The thrombotic activity associated with the antibodies of the invention acts to inhibit platelet aggregation and platelet thrombus formation. Platelets participate in blood coagulation via binding fibrinogen, platelet aggregation and thrombus formation. As anti-thrombotics, these peptides can be useful in the following conditions: myocardial infarction, thromboembolic disease and thrombotic complications due to cancer and cardiovascular disease.

Platelet aggregation is a normal and beneficial process to stop bleeding of damaged tissue. However, platelet aggregation can cause problems following cardiovascular treatment such an angioplasty, thrombolytic therapy or vascular grafting. Platelets contain as much as 25% of the TSP protein in the total alpha granular platelet secreted-protein. Therefore, introduction of an antibody which binds to receptors on the surface of a platelet can prevent the platelet from aggregating and forming a clot.

The antibodies can be useful in numerous therapeutic applications, such as during surgery on peripheral arteries, in cardiovascular surgery or after angioplasty. The antibody can also be used prophylactically to treat and prevent cardiovascular and ischemic disorders and diseases which are associated with platelet aggregation. A drug based on the antibodies of the invention can be used as an adjunct to angioplasty and thrombolytic therapy for use with other clot-dissolving agents which are currently in the market (e.g., tPA, streptokinan). Such an agent does not aggravate bleeding or have the risk of side effects common to synthetic anti-platelet drugs. Additionally, such an antibody can help to keep open small diameter vascular grafts (such as those used in heart by-pass surgery). Similar applications are envisioned for patients at risk for stroke.

The antibodies can also be useful in dialysis applications. The antibodies could be administered to the dialysis patient in an effort to eliminate platelet aggregation on the dialysis membrane. Alternatively, the dialysis membrane could be coated with the antibodies to prevent platelet aggregation as the fluid samples pass through the medical device.

The antibodies of this invention have the ability to specifically inhibit the second stage of platelet aggregation (i.e., the thrombospondin dependent stage of platelet aggregation). This activity allows the antibodies to be useful in inhibiting thrombocytopenia caused as a result of disease state (i.e., Gray Platelet Syndrome, Essential Thrombocythemia, Myeloproliferative Syndrome) or induced by therapy (i.e., cancer therapy) or autoimmune diseases. These antibodies also act to prevent coronary artery reocclusion following balloon catheterization The antibodies of this invention modulate the formation and structure of blood clots. Thrombospondin is incorporated into fibrin clots and serves as a substrate for blood clotting Factor XIIIa. An Ile Aln Aln sequence motif in thrombospondin has been implicated in crosslinking to factor XIIIa. Peptides containing Ile Aln Aln modulate structure and formation of clots. Known fibrinolytic in vitro assays demonstrate this ability.

Antithrombotic activity is characterized by a number of assays, including 1) inhibition of ADP or thrombin-induced platelet aggregation in washed platelets; 2) inhibition of platelet aggregation in platelet-rich plasma; 3) inhibition of collagen induced platelet aggregation measured in vivo; and 4) inhibition of induced thrombus formation in a carotid artery—in this assay the antibody would delay or prevent occlusion of the artery following thrombus induction.

THROMBOLYTIC CONDITIONS

The thrombolytic activity associated with the antibodies of the invention act to alter the structure of a formed thrombus, i.e., dissolution of a blood clot. Thrombolytic activity is characterized as the ability to enhance the dissolution of fibrin in the presence of plasmin (i.e., standard clot lysis assay).

ANGIOGENESIS

Angiogenesis is the formation of blood and lymph vessels. The antibodies of this invention are useful in the modulation of angiogenesis, particularly in enhancing wound healing, inhibiting or preventing tumor growth, diabetic retinopathy, and rheumatoid arthritis. Standard angiogenesis assays are well known in the art. These assays include, but are not limited to, proliferation and migration studies using various cell lines, collagenase inhibition and in vivo neovascularization on chicken chorioallantoic membranes (CAM assay).

ADHESION MODULATION

The antibodies can modulate cell adhesion and inhibit binding of TSP and other proteins to cells, such as blood platelets, which contain the TSP receptor site.

DIAGNOSTIC

Antibodies of the invention can be useful as reagents in diagnostic/prognostic assays for various types of cancer, including but not limited to, gastrointestinal tract (gastric, colonic, and rectal) carcinomas, breast carcinomas and hepatic carcinomas.

CARRIER

Cytotoxic drugs, hormones, or imaging agents can be coupled to the antibodies for use in cancer or other therapy.

BIOMEDICAL DEVICE

A biomedical device can be coated with the antibodies to remove cells which bear receptors for thrombospondin on the cell surface, such as platelets.

The following abbreviations have been used throughout in describing the invention:
TSP—thrombospondin
kd—kilodalton(s)
%—percent
mM—millimolar
$\mu$M—micromolar
ml—milliliter
M—molar
$\mu$l—microliter
FN—fibronectin
BSA—bovine serum albumin
$\mu$g—microgram
g—gram

EXAMPLES

The following examples are presented for illustrative purposes only and are not intended to limit the scope of the invention in any way.

Example 1

Cys Ser Val Thr Cys Gly (SEQ ID NO: 1)-specific Receptor Purification and Characterization A cell extract was prepared from approximately $4.0 \times 10^7$ B$_{16}$-F$_{10}$ mouse melanoma cells or A549 human lung carcinoma cells by dissolving the cell pellet in 5 ml of binding buffer (10 mM Tris-HCl, pH 7.5, containing 0.5% NP-40 detergent, 1 mM CaCl$_2$, 1 mM MgCl$_2$, 100 $\mu$M leupeptin, 1 mM phenylmethyl sulfonyl fluoride (PMSF), 10 $\mu$g/ml aprotinin). Undissolved material was removed from the sample by centrifugation at 4,000$\times$g for 20 min. at 4° C.

A Cys Ser Val Thr Cys Gly (SEQ ID NO: 1) (SEQ ID NO: 1) affinity column was constructed by packing a 5 ml column containing 4 mg of Cys Ser Val Thr Cys Gly (SEQ ID NO: 1) coupled to 1 ml of CN-activated Sepharose equilibrated in HEPES buffered saline, pH 7.35. The extract was applied to the Cys Ser Val Thr Cys Gly (SEQ ID NO: 1) column which had been washed with 50 ml of binding buffer. Nonspecifically adsorbed proteins were removed from the column by washing the column with 50 ml of binding buffer. Specifically adsorbed proteins were eluted with 0.10 M Tris, pH 10.2, containing 0.05% NP-40 detergent, 1 mM CaCl$_2$, 1 mM MgCl$_2$, 100 $\mu$M leupeptin, 1 mM phenylmethyl sulfonyl fluoride (PMSF), and 10$\mu$g/ml aprotinin. Ten ml fractions were collected in tubes containing 700 $\mu$l of 1N HCl to neutralize the Tris. The peak fraction in tube was applied to an anion exchange column (Mono Q, Pharmacia) equilibrated in anion exchange column buffer (20 mM Tris HCl, pH 8.0, containing 5 mM octylglucoside). The bound material was eluted with a 20 ml gradient of NaCl (100% 1M NaCl) and the column monitored at 280 and 260 nM. The bound material routinely began to elute at 0.3M NaCl and the gradient was held to allow the proteins to elute isocratically yielding a single homogenous peak having a high absorbance at 260 nm.

The eluted fraction and unbound fractions were concentrated and the concentrated material analyzed on SDS-gels on an 8% polyacrylamide gel and visualized by comassie blue stain using standard techniques. The peak fraction analyzed on SDS-gel electrophoresis under nonreducing conditions as a major band with an apparent molecular weight of 50 kd and under reducing conditions (5% beta-mercaptoethanol) as two polypeptide bands of 50 and 60 kd, as indicated in FIG. 1 (lanes 1 and 2). Approximately 100 $\mu$g of protein was recovered from $1 \times 10^7$ cells.

The Cys Ser Val Thr Cys Gly (SEQ ID NO: 1)-specific receptor was labelled with $^{125}$I-Iodine by the standard procedure of Karczewski et al. (*J. Biol. Chem.* (1989) 264:21322-6). Briefly, 12 $\mu$g of purified protein dissolved in 100 μl of octylglucoside buffer was incubated with one Iodobead for 5 min. Unreacted iodide was removed on a small column of Sephadex G-25 equilibrated in octylglucoside buffer as previously described by Tuszynski et al. (*Anal. Biochem.* (1980) 106:118–122). The specific activity of protein obtained in a typical experiment was $10^4$ cpm/μg. Analysis of the labelled material by SDS-gel electrophoreses followed by autoradiography indicated that under reducing conditions the 60 kd molecular weight polypeptide band was predominate. The autoradiogram of this labelled material is shown in FIG. 1, lanes 3 and 4.

The labelled $^{125}$I-Cys Ser Val Thr Cys Gly (SEQ ID NO: 1)-specific receptor protein (100,000 cpm) was analyzed on a pH 3–9 isoelectric focusing gel using standard procedures. According to this procedure, the purified material resolved as one band with a pI in the range of about 7.1–7.5 as shown in FIG. 2.

Example 2

Binding Studies

The binding study was performed as follows. Detachable microtiter wells (Immulon 4 Removawell) were coated overnight at 4° C. with either 50 μl of a 40 μg/ml TSP, fibronectin, BSA or peptide solution in 20 mM bis-tris-propane buffer, pH 6.5 and blocked for one hour with 200 μl of 1% BSA. A small aliquot of [$^{125}$I]-labelled Cys Ser Val Thr Cys Gly (SEQ ID NO: 1)-specific receptor was added to binding buffer (20 mM Tris buffered saline, pH 7.35, containing 1 mM CaCl$_2$, 1 mM MgCl$_2$, 0.05% NP40) such that the final concentration was approximately 100,000 cpm per 50 μl of solution (30 nM). 50 μl aliquots were then incubated for one hour in the protein coated wells. Wells were then washed three times by aspiration with 200 μl of binding buffer and bound radioactivity determined by counting each well in a gamma counter. The Cys Ser Val Thr Cys Gly (SEQ ID NO: 1)-specific receptor protein had the greatest binding affinity for TSP and Cys Ser Val Thr Cys Gly (SEQ ID NO: 1) since fibronectin, BSA, and VCTGSC, a peptide control for Cys Ser Val Thr Cys Gly (SEQ ID NO: 1), bound 46%, 37%, and 27% as much as was observed for TSP. These results indicate that the Cys Ser Val Thr Cys Gly (SEQ ID NO: 1)-specific receptor protein can interact specifically with TSP in vitro. Approximately, one μg of labelled receptor bound 1μg of immobilized TSP. TSP bound three times more labelled receptor than did FN or BSA.

Example 3

Surface Labelling of Receptor

Intact, growing A549 cells were surface labelled with [125]-Iodine using lactoperoxidase as described by Tuszynski et al. (*Anal. BioChem.* (1980) 106:118–122). Briefly, a 75 mm flask containing a near confluent monolayer of cells was rinsed three times with 10 ml of DMEM. Then the cell layer was covered with 5 ml of DMEM containing 0.2 units/ml lactoperoxidase and 500 μCi of [125]-iodide. Five one μl aliquotes of 30% H$_2$O$_2$ were added with gentle mixing at one minute intervals. The reaction was then stopped by the addition of 5 μl of a 1 mM NaN$_3$, the monolayer washed three times with DMEM, and cells harvested for purification of CSVTCG binding proteins.

Analysis of the labeled material by SDS-gel electrophoresis followed by autoradiography revealed that the $M_r = 50,000$ polypeptide under non-reduced conditions labelled by in vitro iodination was labelled (FIG. 1, lane 5).

The receptor bound TSP in a time-dependent manner which became time-independent after 60 min. The binding was maximal in the presence of both 1 mM CaCl$_2$ and 1 mM MgCl$_2$ and whereas a small but significant amount of binding occurred in the presence of 1 mM EDTA.

Example 4

Receptor Antibodies

Polyclonal Cys Ser Val Thr Cys Gly (SEQ ID NO: 1)-specific receptor antiserum was raised in a rabbit by standard procedures after four 50 μg injections every three to four weeks. The first injection was given with complete Freund's adjuvant and subsequent injections were administered with incomplete Freund's adjuvant. Antibody titers and specificity were determined by ELISA.

ELISA assays were performed following standard procedures. Briefly, microtiter plates were coated with 2 μg of Cys Ser Val Thr Cys Gly (SEQ ID NO: 1)-specific receptor, fibronectin or BSA and blocked with 1% BSA for 1 hour. Wells were incubated for 1 hr with 50 μl of various dilutions of the first antibody in 10 mM phosphate buffer, pH 7.4, containing 150 mM NaCl and 0.05% Tween-20 (PBS-T). Wells were then washed three times in PBS-T and incubated for 1 hr with 50 μl of a 1:800 dilution in PBS-T of alkaline phosphatase coupled rabbit anti-goat IgG. Wells were washed three times with PBS-T followed with three washes of PBS-T buffer containing no Tween-20 ® and treated with 50 μl of alkaline phosphatase substrate solution (1 mg/ml of p-nitrophenylphosphate in 0.10M glycine, pH 10.4, containing 1 mM ZnCl$_2$ and 1 mM MgCl$_2$). After 30 minutes, color development was stopped by the addition of 5 μl of 1N NaOH and absorbances determined at 405 nm.

The antibody was monospecific as determined by direct ELISA as shown in Table I.

TABLE I

| | Absorbance (405 nm) | | |
|---|---|---|---|
| | BSA | Fibronectin | CSVTCG Specific Receptor |
| Preimmune Serum | 0.123 ±0.005 | 0.135 ±0.006 | 0.130 ±0.0007 |
| Anti- Cys Ser Val Thr Cys Gly (SEQ ID NO: 1) Specific Receptor | 0.134 ±0.007 | 0.176 ±0.004 | 0.665 ±0.003 |

Example 5

Lectin Study

The following lectin study was performed to determine that carbohydrates are present on the CSVTCG-specific receptor. Lectins were coated in microtiter wells by incubating each well with 100 μl of a 40 μ/ml solution of lectin in PBS. Wells were washed twice in PBS, blocked with BSA, and incubated with 50 μl of [$^{125}$I]-Cys Ser Val Thr Cys Gly (SEQ ID NO: 1)-specific receptor protein in binding buffer. Wells were washed twice in PBS and bound radioactivity counted. Table II shows the results which indicate that the receptor bound galactose, mannose and glucosamine-specific lectins.

TABLE II

| Lectin CSVTCG Binding Protein Interactions | | |
|---|---|---|
| Lectin | Counts Bound | Sugar Specificity |
| Con A | 1264 | alpha-D-man, glucose |
| Lens culinaris | 896 | alpha-D-man |
| Lycopersicon esculentum | 2140 | (D-glcNAc)$_3$ |
| Ptilota plumosa | 1112 | alpha-D-gal |
| Dolichos biflorus | 379 | alpha-D-galNAc |
| Tetragonolobus purpureas | 641 | alpha-L-fuc |

Example 6

Adhesion Inhibition by Antibody

The following experiment was performed to determine the ability of the anti-Cys Ser Val Thr Cys Gly (SEQ ID NO: 1)-specific receptor antibody to inhibit adhesion of cancer cells to TSP. Detachable microtiter wells (Immulon 4 Removawell) were coated overnight at 4° C. with either 50 μl of a 40 μg/ml TSP, fibronectin, or laminin solution in 20 mM bis-tris-propane buffer, pH 6.5 and blocked for one hour with 200 μl of 1% BSA. A549 cells and 200 μg/ml of IgG for anti-Cys Ser Val Thr Cys Gly (SEQ ID NO: 1)-specific receptor or non-immune antisera were incubated for 30 minutes and centrifuged to remove unbound antibody. The pellet was resuspended in DMEM and the cells incubated in the protein-coated wells for 60 minutes at 37° C. The number of cells adhering to the microtiter well surface was counted. The results in Table III are presented as % of non-immune IgG-treated adherent cells. Table III shows that anti-Cys Ser Val Thr Cys Gly (SEQ ID NO: 1)-specific receptor antibody inhibits A549 cell adhesion to TSP-coated surfaces, but had no effect on cell adhesion to fibronectin or laminin. The antibody also inhibited adhesion of TSP to the tissue culture plastic.

Example 7

The Effect of Antibodies on Tumor Cell Metastasis

The CVSTCG-specific receptor antibodies described in Example II are used to demonstrate in vivo the ability to inhibit tumor cell metastasis.

The in vivo model used to demonstrate the antimetastatic activity of the peptide compounds of the invention is described by Tuszynski et al. (*Cancer Res.* (1987) 47:4130–4133). Briefly, C57 black mice are intravenously injected with $1\times10^5$ $B_{16}F_{10}$ mouse melanoma cells in the presence of either 100 μg IgG, or 100 μg anti-Cys Ser Val Thr Cys Gly (SEQ ID NO: 1)-specific receptor antibody of the invention. Five or six animals are used for each compound. Antibodies tested in the assay have no effect on cell viability as measured by Trypan blue dye exclusion. In addition, the antibodies do not effect cell growth after 24 hours of co-culture. After 14 days, the mice are sacrificed and the number of lung tumors counted.

The antibodies of the invention are effective in inhibiting metastatic activity.

Example 8

The Effect of Antibodies on Platelet Aggregation

Platelet aggregation is monitored on a single-channel aggregometer equipped to measure luminescence (Chromo-Log, Hayertown, Pa.). Platelet-rich-plasma (PRP) is obtained from whole blood anti-coagulated with 0.38 sodium citrate by centrifugation at 150× g for 20 minutes. 0.5 ml aliquots of platelet-rich-plasma are aggregated by stirring with 2 μM ADP in the presence of various concentrations of control IgG or anti-Cys Ser Val Thr Cys Gly (SEQ ID NO: 1)-specific receptor antibody. Aggregation is measured at 37° C. as decrease in optical absorbance vs. time in a chrono-log aggregometer. The antibodies of the invention are effective in inhibiting platelet aggregation.

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 6 amino acids
( B ) TYPE: amino acid
( D ) TOPOLOGY: linear ( i i ) MOLECULE TYPE: peptide ( x i ) SEQUENCE DESCRIPTION: SEQ ID NO:1:

Cys Ser Val Thr Cys Gly
1 5

TABLE III

| Protein Substrate | % Adhering Cells |
|---|---|
| Thrombospondin | 10.5% |
| Fibronectin | 101% |
| Laminin | 103% |

We claim:

1. A purified receptor protein capable of specifically binding the hexapeptide Cys Ser Val Thr Cys Gly (SEQ ID NO: 1) having the following properties:

(i) a molecular weight of about 50 kD determined by SDS-PAGE under non-reducing conditions;

(ii) two proteins of molecular weights of about 50 kD and 60 kD determined by SDS-PAGE under reducing conditions;

(iii) an isoelectric focus point ranging from about 7.1–7.5; and (iv) a glycoprotein comprising two subunits linked by intrachain disulfide bonds.

2. The receptor protein of claim 1 which has been purified by a process comprising:

(i) obtaining a cell extract from a tumor cell which comprises Cys Ser Val Thr Cys Gly (SEQ ID NO: 1) specific receptors;

(ii) applying said cell extract to a chromatographic column to which is immobilized a Cys Ser Val Thr Cys Gly (SEQ ID NO: 1) peptide under conditions wherein the Cys Ser Val Thr Cys Gly (SEQ ID NO: 1) receptor protein specifically binds to said immobilized peptide; and (iii) eluting the specifically bound receptor protein from the column to provide a purified Cys Ser Val Thr Cys Gly (SEQ ID NO: 1) binding receptor protein.

3. The receptor protein of claim 2 wherein the tumor cell is selected from the group consisting of melanoma and lung carcinoma cells.

4. The receptor protein of claim 2 which is further subjected to an additional purification step comprising applying said eluted purified receptor protein through an anion exchange column.

* * * * *